United States Patent
Souentie et al.

(10) Patent No.: US 9,951,430 B2
(45) Date of Patent: Apr. 24, 2018

(54) METHODS FOR CO-PROCESSING CARBON DIOXIDE AND HYDROGEN SULFIDE

(71) Applicant: Saudi Arabian Oil Company, Dhahran (SA)

(72) Inventors: Stamatios Souentie, Dhahran (SA); Alberto Lozano Ballesteros, Dhahran (SA); Fritz Simeon, Abqaiq (SA)

(73) Assignee: Saudi Arabian Oil Company, Dhahran (SA)

( * ) Notice: Subject to any disclaimer, the term of this patent is extended or adjusted under 35 U.S.C. 154(b) by 168 days.

(21) Appl. No.: 14/688,578

(22) Filed: Apr. 16, 2015

(65) Prior Publication Data

US 2016/0305029 A1   Oct. 20, 2016

(51) Int. Cl.
*H01M 8/06* (2016.01)
*C25B 1/02* (2006.01)
(Continued)

(52) U.S. Cl.
CPC .............. *C25B 1/02* (2013.01); *C07C 1/12* (2013.01); *C25B 1/00* (2013.01); *C25B 5/00* (2013.01);
(Continued)

(58) Field of Classification Search
CPC ........ H01M 8/0637; H01M 8/22; H01M 8/06; H01M 8/0606; H01M 8/0625;
(Continued)

(56) References Cited

U.S. PATENT DOCUMENTS

| 3,409,520 A | 9/1965 | Bolmer |
| 3,249,522 A * | 5/1966 | Bolmer .................. C01B 17/34 |
| | | 205/343 |

(Continued)

FOREIGN PATENT DOCUMENTS

| UA | 61556 U | 7/2011 |
| UA | 62880 U | 9/2011 |
| UA | 99863 C2 | 10/2012 |

OTHER PUBLICATIONS

International Search Report and Written Opinion dated Feb. 9, 2016 for PCT/US2015/055492 filed Oct. 14, 2015. pp. 1-13.
(Continued)

*Primary Examiner* — Raymond Alejandro
(74) *Attorney, Agent, or Firm* — Dinsmore & Shohl LLP

(57) ABSTRACT

A method for co-processing $H_2S$ and $CO_2$ in an electrolyzer includes feeding a first gas stream having $H_2S$ to an anode and feeding a second gas stream having $CO_2$ to a cathode. The $H_2S$ is split into hydrogen and elemental sulfur. The hydrogen is transferred from the anode to the cathode, and the $CO_2$ is hydrogenated with the transferred hydrogen. A method for producing electricity in a fuel cell includes feeding a first gas stream having $H_2S$ and CO to an anode, and feeding a second gas stream having oxygen to a cathode. The $H_2S$ and CO forms hydrogen and carbonyl sulfide. The hydrogen is transferred from the anode to the cathode. The transferred hydrogen is oxidized with the oxygen of the second gas stream, and electricity formed from the oxidation is collected.

12 Claims, 8 Drawing Sheets

(51) Int. Cl.

| | | |
|---|---|---|
| *C25B 1/00* | (2006.01) | |
| *C25B 5/00* | (2006.01) | |
| *C25B 9/08* | (2006.01) | |
| *H01M 8/22* | (2006.01) | |
| *C07C 1/12* | (2006.01) | |
| *H01M 8/0637* | (2016.01) | |

(52) U.S. Cl.
CPC ............ *C25B 9/08* (2013.01); *H01M 8/0637* (2013.01); *H01M 8/22* (2013.01); *Y02E 60/566* (2013.01)

(58) Field of Classification Search
CPC .... H01M 8/0675; H01M 8/0687; H01M 8/18; H01M 8/184; C25B 1/02; C25B 1/00; C25B 5/00; C25B 9/08
See application file for complete search history.

(56) References Cited

U.S. PATENT DOCUMENTS

| | | | |
|---|---|---|---|
| 4,081,337 A | 3/1978 | Spitzer | |
| 4,544,461 A | 10/1985 | Venkatesan et al. | |
| 4,859,292 A | 8/1989 | Appleby | |
| 5,019,227 A | 5/1991 | White et al. | |
| 5,140,049 A | 8/1992 | Fiato et al. | |
| 5,393,793 A | 2/1995 | Inue | |
| 5,578,189 A | 11/1996 | Joshi | |
| 6,241,871 B1 | 6/2001 | Donini et al. | |
| 7,278,068 B1 | 10/2007 | Crowder, Jr. | |
| 7,378,068 B2 | 5/2008 | Mao et al. | |
| 7,985,332 B2 | 7/2011 | Greaney et al. | |
| 2003/0215696 A1 | 11/2003 | Chuang et al. | |
| 2012/0055808 A1 | 5/2012 | Martin et al. | |

OTHER PUBLICATIONS

J. Mbah, B. Krakow, E. Stefanakos and J. Wolan, Electrolytic Splitting of H2S using CsHSO4 membrane, J. Electrochemical Society, 155(11) (2008) E166-E170.

J. Mbah, S. Srinivasan, B. Krakow, J. Wolan, Y. Goswami, E. Stefanakos and N. Appathurai, Effect of RuO2—CoS2 anode nanostructured on performance of H2S Electrolytic splitting system, J. Electrochemical Society, 155(11) (2008) E166-E170.

L Aguilar, S. Zha, Z. Cheng, J. Winnick and M. Liu, A solid oxide fuel cell oeprating on hydrogen sulfide (H2S) and sulfur-containing fuels, J. Power Sources 135 (2004) 17-24.

V. Vorontsov, J.L. Luo, A.R. Sanger and K.T. Dhuang, Synthesis and characterization of new ternary transition metal sulfide anodes for H2S-powered solid oxide fuel cells, J. Power Sources 183 (2008) 76-83.

K.T. Chuang, A.R. Sanger, S.V. Slavov and J.C. Donini, A proton-conducting solid state H2S—O2 fuel cell; Operation using H2S-hydrocarbon mixtures as anode feed, Int. J. of Hydrogen Energy 26 (2001) 103-108.

\* cited by examiner

US 9,951,430 B2

METHODS FOR CO-PROCESSING CARBON DIOXIDE AND HYDROGEN SULFIDE

BACKGROUND

Field

The present specification generally relates co-processing carbon dioxide ($CO_2$) and hydrogen sulfide ($H_2S$). More particularly, the present specification is directed to electrochemical methods for producing high-value chemicals by co-processing byproduct streams of $CO_2$ and $H_2S$.

Technical Background

Hydrogen sulfide and carbon dioxide are two common compounds that are present in some naturally occurring hydrocarbon deposits. These compounds are generally removed from the hydrocarbon and are of low value as extracted. Therefore, $H_2S$ and $CO_2$ are generally either discarded or further processed into various compounds of more value. Currently, $CO_2$ and $H_2S$ are separately processed, which leads to higher overhead costs and other inefficiencies.

Accordingly, systems and methods that enable more efficient treatment of $H_2S$ and $CO_2$ that is removed from hydrocarbon feeds are desired.

SUMMARY

According to some embodiments, a method for co-processing $H_2S$ and $CO_2$ in an electrolyzer is disclosed. The electrolyzer comprises an anode, a cathode, and an electrolyte positioned between and in electrochemical contact with the anode and the cathode. The method according to embodiments comprises: feeding a first gas stream comprising $H_2S$ to the anode of the electrolyzer; feeding a second gas stream comprising $CO_2$ to the cathode of the electrolyzer; splitting $H_2S$ of the first gas stream into hydrogen and elemental sulfur; transferring the hydrogen split from the $H_2S$ of the first gas stream from the anode across the electrolyte to the cathode; and hydrogenating the $CO_2$ from the second gas stream with the hydrogen that was transferred from the anode.

According to other embodiments, a method for producing electricity in a fuel cell is disclosed. The fuel cell comprises an anode, a cathode, and an electrolyte positioned between and in electrochemical contact with the anode and cathode. The method according to embodiments comprises: feeding a first gas stream comprising $H_2S$ and CO to the anode; feeding a second gas stream comprising oxygen to the cathode; splitting the $H_2S$ from the first gas stream into hydrogen and elemental sulfur; forming carbonyl sulfide from the elemental sulfur split from the $H_2S$ of the first gas stream and the CO of the first gas stream; transferring the hydrogen split from the $H_2S$ of the first gas stream from the anode across the electrolyte to the cathode; oxidizing the hydrogen that is transferred from the anode across the electrolyte to the cathode with the oxygen of the second gas stream; and collecting electricity formed from the oxidizing of the hydrogen that is transferred from the anode across the electrolyte to the cathode.

According to yet other embodiments, another method for co-processing $H_2S$ and $CO_2$ in an electrolyzer is disclosed. The electrolyzer comprises an anode, a cathode, and an electrolyte positioned between and in electrochemical contact with the anode and cathode. The method according to embodiments comprises: feeding a first gas stream comprising $H_2S$ and $CO_2$ to the anode; splitting the $H_2S$ from the first gas stream into hydrogen and elemental sulfur; forming SOx and CO from the elemental sulfur split from the $H_2S$ of the first gas stream and the $CO_2$ of the first gas stream; transferring the hydrogen split from the $H_2S$ of the first gas stream from the anode across the electrolyte to the cathode; exhausting the hydrogen transferred from the anode across the electrolyte to the cathode from the electrolyzer consuming electricity.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
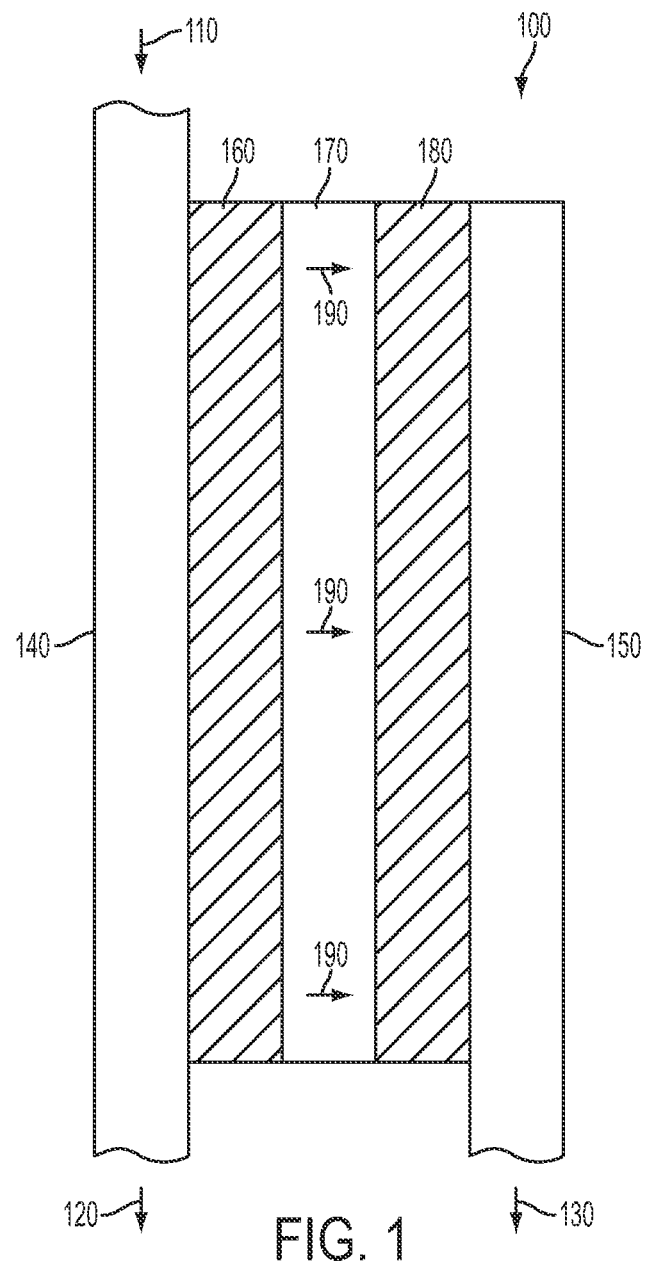
FIG. 1 schematically depicts a conventional electrolysis unit for treating $H_2S$.

Methods for treating $H_2S$ and $CO_2$ separately are disclosed below. These methods generally require significant amounts of energy and are inefficient compared to embodiments disclosed herein. While the below methods are described in detail and with specific reaction mechanisms, it should be understood that various other reaction mechanisms may occur and fall within the scope of this disclosure.

Methods for processing $H_2S$ involve Claus reactions that use high temperatures to oxidize $H_2S$ to $SO_2$ and then further to elemental sulfur. For example, in a Claus unit gaseous H₂S generally undergoes a substoichiometric combustion at temperatures of about 1,000° C. to form gaseous SO₂ that then reacts with uncombusted gaseous H₂S to form elemental sulfur, as shown in reactions (1) and (2) set forth below:

$$H_2S(g) + 3/2\, O_2(g) \xrightarrow{1000°\,C.} SO_2(g) + H_2O(g); \quad (1)$$

$$2H_2S(g) + SO_2(g) \xrightarrow{200\text{-}300°\,C.} 3/2\, S_2(l) + 2H_2O(g). \quad (2)$$

Diatomic S₂, as formed in the above reactions, is highly reactive and reacts primarily with other diatomic S₂ to form an S₈ allotrope as shown in reaction (3) below:

$$4S_2 \rightarrow S_8 \quad (3).$$

As shown in reactions (2) and (3) above, the recovery of elemental sulfur from H₂S comprises three sub-steps: heating a mixture of H₂S and SO₂ to a temperature from about 200° C. to about 300° C.; a catalytic reaction; and cooling plus condensation. These three sub-steps are generally repeated up to three times to convert a maximum amount of H₂S to elemental sulfur and water. These reactions are exothermic and a portion of the reaction energy may be recovered as low-grade energy, such as by producing steam or the like. However, the energy capture is not very efficient.

In conventional treatments, when CO₂ is present in the gas feed, the same reaction processes shown in reactions (1)-(3) above may be used. In such a case, the CO₂ is inert and does not react or combust with the other constituents. Thus, in conventional treatments CO₂ exits the reaction unit without reacting, and is discarded or further treated. This leads to inefficiencies by requiring additional units and further processing.

In reactions (1)-(3) shown above, the Claus process converts hydrogen atoms of H₂S into steam via an oxidation reaction. As shown above, the Claus reactions do not produce very useful products, and the above reactions cannot be used to treat CO₂ that may be present in the feed stream, or that is exhausted from a CO₂ capture unit.

Another conventional method for treating H₂S is the Stenger-Wasas Process (SWAP) developed by SWAPSOL Corp. In SWAP, H₂S and CO₂ are reacted to form water, sulfur, heat, and carsul (a black insoluble material formed by the reaction between carbon and sulfur). The carsul formed by SWAP can then be heated to produce carbon-based monomers and sulfur. SWAP may be used as an alternative of the Claus process described by Reactions (1)-(3) above, and can be applied to flue gasses, sour gasses, landfill gasses, Claus tail gasses, hydrocarbon waste recycling, and the like. A reaction mechanism for SWAP is shown in reaction (4) below:

$$CO_2(g) + H_2S(g) \rightarrow S + H_2O + carsul + heat \quad (4).$$

Although SWAP does treat a feed comprising both CO₂ and H₂S, it produces intermediary components that are not very useful and should be further processed into usable chemicals.

As an alternative of, or in addition to, the above chemical reactions for processing H₂S, electrochemical processes may be used. Electrochemical processes according to embodiments may be carried out using an electrolysis unit, such as the electrolysis unit depicted in FIG. 1. In the electrolysis unit of FIG. 1 a proton conducting electrolyte membrane is used to split H₂S into elemental sulfur (S$_n$, where n is from 2 to 8) at an anode and diatomic hydrogen (H₂) at the cathode.

With reference now to FIG. 1, an electrolysis unit 100 comprises a feed gas channel 140 where a feed gas 110 comprising H₂S is fed into the electrolysis unit 100. The feed gas 110 is fed into the electrolysis unit 100 at the anode 160 side of the electrolysis unit 100. The anode 160 is positively charged and splits the H₂S in the feed gas into elemental sulfur and hydrogen atoms. The hydrogen atoms migrate across an electrolyte 170, as shown by arrows 190, toward the negatively charged cathode 180, and gaseous diatomic hydrogen is formed. The gaseous hydrogen enters an exhaust channel 150 of the electrolysis unit 100 and is then exhausted from the exhaust channel as shown by arrow 130. Elemental sulfur exits the electrolysis unit 100 at the end of the feed channel 140, as shown by arrow 120. A reaction mechanism that occurs at the anode 160 is shown in reaction (5) below, and a reaction mechanism that occurs at the cathode 180 is shown in reaction (6) below:

$$H_2S(g) \rightarrow 2H^+ 1/nS_n + 2e^- \quad (5);$$

$$2H^+ + 2e^- \rightarrow H_2(g) \quad (6).$$

To achieve the above electrolysis of H₂S, specific anodes 160 and electrolytes 170 that facilitate the treatment of feed gases comprising H₂S are used. For example, platinum is a common anode catalyst material because it generally has good catalytic activity (i.e., it has good H₂S adsorption). However, platinum degrades over time when exposed to feed gases comprising H₂S and, thus, is not a preferable anode material for electrolyzer designed to treat H₂S. Likewise, many other metal oxides commonly used as anode materials degrade rapidly when exposed to H₂S. Thus, in embodiments, other anode materials are used. For instance, in embodiments the anode may comprise a metal sulfide, such as, for example, Li₂S/CoS₁.₃₅ WS₂, NiS, MoS₂, CoS, VO₅, LiCoO₂, Pt/TiO₂, Pd, Au, Ag, Ru, Rd, Ir, FeMoS, NiMoS, CoMoS and mixtures thereof. In embodiments, Ni-based compounds may be used as anode materials, such as Nb₂O₅—Ni, BaO—Ni, Ce₀.₈Sm₀.₂O₂—Ni. In embodiments, thiospinels may be used as anode materials, such as CuFe₂S₄, CuNi₂S₄, CuCoS₄, NiCo₂S₄, NiFe₂S₄, and mixed metal oxides of La, Sr, Mn, Ti, Cr, Ga, Y, V, Fe, Co, Mo, Ce, Mg, Gd, and Ba (e.g. La₀.₄Sr₀.₆BO₃, where B=Mn, Ti, Cr). Most of the above-mentioned materials have been reported to exhibit electrochemical activity for H₂S utilization in both fuel cells and electrolyzers. According to embodiments, the above materials can be used either as is or in mixture with another oxide in the form of ceramic-metallic (cermet) electrode. In embodiments comprising cermet electrodes, oxides that conduct oxygen or protons can be used, such as YSZ, ScSZ, ScYSZ, GDC, CGO, CeO₂, TiO₂, Nb₂O₅, SDC, BCY, CZI, BCN, or the like.

Although many electrolytes that transmit H⁺ may be used as the electrolyte 170 in the electrolysis unit 100, in embodiments the electrolyte 170 is chosen according to its proclivity to treat H₂S, such as a resistance to sulfur degradation. In general, perovskite materials of the general type ABO₃ and ABMO₃ exhibit proton conductivity at high temperatures (600-1000° C.). In some embodiments, zirconia-based electrolytes are used in the electrolysis unit, such as SrZrO₃ and NiO-doped BZY. In other embodiments, ceria-based electrolytes are used in the electrolysis unit, such as BaCeO₃, SrCeO₃ or YDC, SDC, BCY, BCN and CZI. In yet other embodiments, the electrolyte may be a solid acid of the general type MHXO₄ and M₃H(XO₄)₂, where M can be Cs, NH$_4$, Rb, and X can be S or Se. These materials exhibit protonic conductivity at low temperatures, in the range 25 to 300° C. and are known to undergo a "superprotonic" phase transition.

In addition to the above treatment options for H$_2$S, it can be used in solid oxide fuel cells to produce electric energy. Two types of fuel cells may be used with H$_2$S; fuel cells comprising oxygen-conducting solid electrolytes and fuel cells comprising proton-conducting solid electrolytes.

Figure 2A:
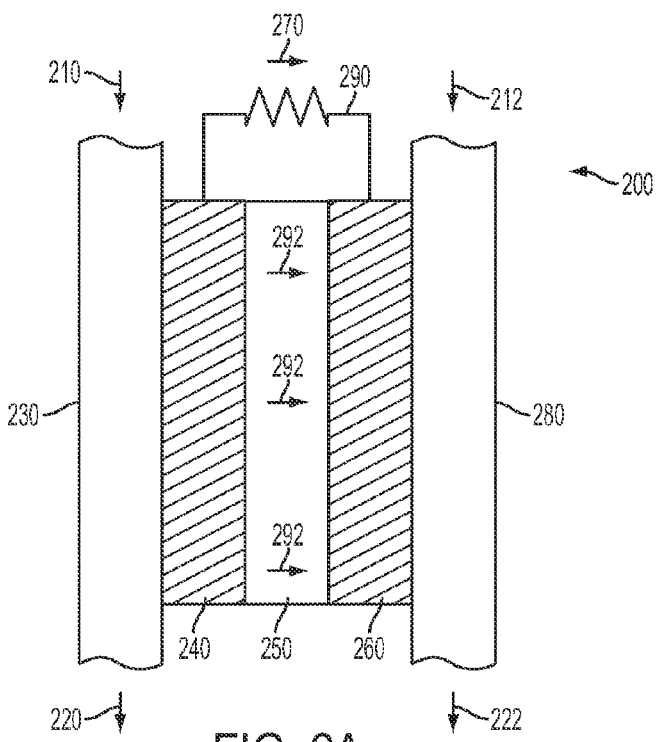
FIGS. 2A and 2B schematically depict conventional $H_2S$ fuel cells.

FIG. 2A shows a solid oxide fuel cell 200 with a proton conducting solid electrolyte 250. The fuel cell 200 includes a first feed channel 230 and a second feed channel 280. Between the first feed channel 230 and the second feed channel 280 are an anode 240, a cathode 260, and the electrolyte 250 between, and in electrochemical contact with, the anode 240 and the cathode 260. The anode, 240, electrolyte 250, and cathode 260 are constructed so that protons can be transferred from the anode 240 through the electrolyte 250 and to the cathode 260. The fuel cell 200 also comprises an electrical connection 290 between the anode 240 and the cathode 260.

In operation, the solid oxide fuel cell depicted in FIG. 2A is fed a gas stream 210 comprising H$_2$S at the first feed channel 230 and air 212 is fed to the second feed channel 280. At the anode 240 the H$_2$S is anodically oxidized to H$^+$ and elemental sulfur S$_n$ as shown in Reaction (7) below:

$$H_2S(g) \rightarrow 2H^+ + 1/nS_n + 2e^- \qquad (7).$$

The protons (H$^+$) formed in Reaction (7) are transferred from the anode 240 through the electrolyte 250 to the cathode 260, as shown by arrows 292. The electrons formed by Reaction (7) are transferred by the electrical connection 290 between the anode 240 and the cathode 260, as shown by arrow 270. The Elemental sulfur S$_n$ 220 formed by Reaction (7) exits the fuel cell via the first feed channel 230.

At the cathode 260 the H$^+$ ions are oxidized by the oxygen in the fed air 212 and water is produced, as shown in Reaction (8) below:

$$2H^+ + \tfrac{1}{2}O_2 + 2e^- \rightarrow H_2O(g) \qquad (8).$$

A mixture 222 of the gaseous H$_2$O produced by Reaction (8) and the unreacted air exit the fuel cell 200 at the second feed channel 280.

Figure 2B:
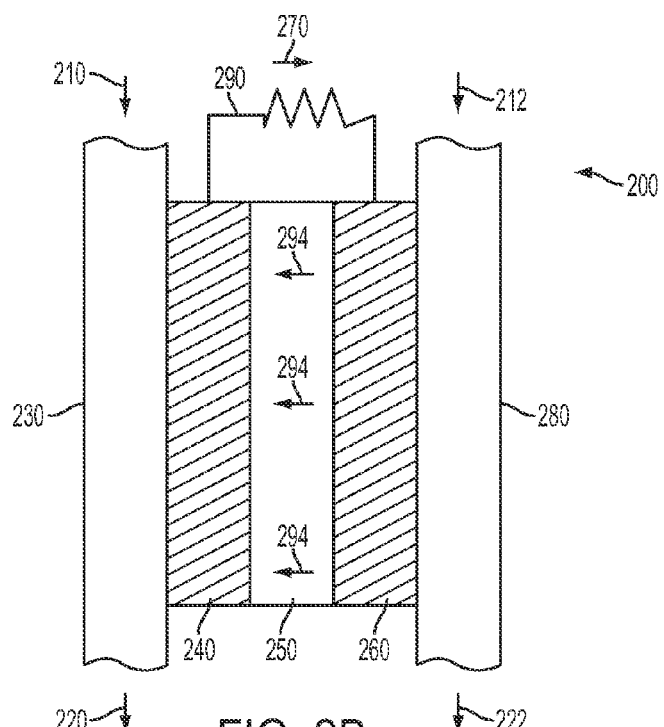

FIG. 2B shows a solid oxide fuel cell 200 with an oxygen-ion conducting solid electrolyte 250. The fuel cell 200 includes a first feed channel 230 and a second feed channel 280. Between the first feed channel 230 and the second feed channel 280 are an anode 240, a cathode 260, and the electrolyte 250 between, and in electrochemical communication with, the anode 240 and the cathode 260. The anode, 240, electrolyte 250, and cathode 260 are constructed so that oxygen ions can be transferred from the cathode 260 through the electrolyte 250 and to the anode 240. The fuel cell 200 also comprises an electrical connection 290 between the anode 240 and the cathode 260.

In operation, the solid oxide fuel cell depicted in FIG. 2B is fed a gas stream 210 comprising H$_2$S at the first feed channel 230 and air 212 is fed to the second feed channel 280. At the cathode 260 oxygen from the air is ionized, as shown in Reaction (9) below:

$$\tfrac{1}{2}O_2(g) + 2e^- \rightarrow O^{2-} \qquad (9).$$

The oxygen ions formed in Reaction (9) transfer from the cathode 260 through the electrolyte 250 to the anode 240, as shown by arrows 294. Unreacted air 222 exits the fuel cell 200 at the second feed channel 280.

At the anode 240 the O$^{2-}$ ions, which were transferred from the cathode 260 and through the electrolyte 240, react with the H$_2$S to form elemental sulfur (S$_n$), SO$_x$, and H$_2$O, as shown in Reactions (10) and (11) below:

$$H_2S(g) + O^{2-} \rightarrow H_2O + \tfrac{1}{8}S_8 + 2e^- \qquad (10);$$

$$H_2S(g) + 3O^{2-} \rightarrow H_2O + SO_2 + 6e^- \qquad (11).$$

A mixture 222 of the gaseous H$_2$O, SO$_x$, and elemental sulfur produced by Reactions (10) and (11) exit the fuel cell 200 at the first feed channel 230. The electrons formed by Reactions (10) and (11) are transferred from the anode 240 to the cathode 260 via the electrical connection 290, as shown by arrow 270.

Although fuel cells using a proton transferring solid oxide electrolyte and an oxygen ion transferring solid oxide electrolyte can both be used, the power efficiency per mole of H$_2$S is higher in the oxygen ion transferring electrolyte because both the hydrogen and the sulfur atoms act as fuel and are electrochemically oxidized to produce electricity. Solid metal sulfide-based catalyst electrodes, such as MoS$_2$ or WS$_2$, may be used as electrodes, particularly the anode, in the fuel cells disclosed above.

The above processes are conventional treatments for H$_2$S that split the H$_2$S in a feed stream to form elemental sulfur and hydrogen. As disclosed above, splitting of H$_2$S results in products that can either be reused, or in the formation of electricity in the case of a fuel cell. However, as disclosed above, these processes can be inefficient by requiring large amounts of energy.

Like H$_2$S, CO$_2$ is present in many hydrocarbon deposits and is receiving attention as a pollutant. It is expected that CO$_2$ will be more heavily regulated in the near future. Accordingly, processes that convert CO$_2$ into usable chemicals are desired. One such process is CO$_2$ hydrogenation, where CO$_2$ is hydrogenated to usable chemicals such as, for example, hydrocarbons, monomers or polymers, and oxygenates. Hydrogenation of CO$_2$ to hydrocarbons or alcohols is attractive because it is a potential source of renewable fuels while decreasing CO$_2$ emissions.

Many CO$_2$ hydrogenation processes use metal catalysts, such as, for example, Pt, Rh, Pd, Ru, Cu, Fe, Co, and Ni. The hydrogenation process takes place in fixed bed reactors where the metal catalysts are supported by metal oxide supports, such as, for example, Nb$_2$O$_3$, ZrO$_2$, Al$_2$O$_3$, and SiO$_2$. The catalytic hydrogenation generally operates at high pressure (such as, for example, from about 5 to about 70 atm, or from about 10 to about 60 atm, or even from about 20 to about 50 atm) to increase the thermodynamic equilibrium conversion to light hydrocarbons or alcohols, such as methanol. The two main reactions that take place during the catalytic hydrogenation are shown in reactions (12) and (13) below:

$$CO_2(g) + H_2(g) \xrightarrow{T,\,P,\,\text{catalyst}} CO(g) + H_2O(g); \qquad (12)$$

$$xCO_2 + (2x - z + y/2)H_2(g) \xrightarrow{T,\,P,\,\text{catalyst}} C_xH_yO_z(g) + (2x - z)H_2O(g). \qquad (13)$$

In the above, Reaction (12) takes place at temperatures from about 300° C. to about 1000° C. and is favored at higher temperatures, and Reaction (13) takes place at lower temperatures, such as from about 200° C. to about 800° C., depending on the desired product ($C_xH_yO_z$). Reviewing the reaction temperature ranges of Reactions (12) and (13) interestingly shows the importance of using intermediate-temperature electrolysis and fuel cell devices, such as devices that operate from about 500° C. to about 700° C.

Reaction (12) above is a redox reaction that constitutes a reverse water-to-gas shift reaction. Reaction (13) above is a synthesis reaction that leads to the formation of hydrocarbons (such as, for example, methane, ethane, propane, etc.), alcohols (such as methanol, ethanol, propanol, etc.), or both. For example, in Reaction (13), methane is formed when x=1, y=4, and z=0, but methanol is formed when x=1, y=4, and z=1. An advantage of using gaseous catalytic hydrogenation reactions, such as those shown in Reactions (12) and (13), over liquid-based hydrogenation reactions is that they have relatively high reaction rates that are comparable with other industrial processes (i.e., the hydrogenation reactions consistently produce product). Thus, such gaseous hydrogenation reactions can reliably be used to hydrogenate $CO_2$ into more useful chemicals, such as hydrocarbons, polymers, and alcohols.

In addition to the chemical hydrogenation of $CO_2$ shown above, electrochemical processes can be used in a reduction-conversion reaction with $CO_2$. Such processes can generally convert liquid phase-dissolved $CO_2$ into more usable chemical products. In these electrochemical processes $CO_2$ is dissolved into solvent, such as water or another primarily aqueous solvent, and is electrochemically reduced at a cathode. Suitable cathode materials include Cu, Ag, Pd, or Rh. However, electrochemical hydrogenation of gaseous $CO_2$ may also be used, but has previously been limited to co-electrolysis of $CO_2$ and $H_2O$ to syngas (CO and $H_2$). Reactions (14) and (15) below show gaseous hydrogenation:

$$CO_2(g) + 2e^- \rightarrow CO(g) + O^{2-} \quad (14);$$

$$H_2O(g) + 2e^- \rightarrow H_2(g) + O^{2-} \quad (15).$$

In addition to the above electrochemical reduction-conversion reaction, electrochemical processes can be used to promote the catalytic hydrogenation of $CO_2$, which is shown in Reactions (12) and (13). In these processes, a constant current or potential is provided between a working electrode, which may also be acting as a catalyst, and a counter or reference electrode. Such a current or potential causes a migration of promoting species (ionic species accompanied by their mirror charge in the catalyst) from an electrolyte support to a catalyst/gas phase interface. These promoting species promote the catalytic gas phase reaction. For example, in Reactions (12) and (13), the electrochemically produced proton species can promote the catalytic reaction in a reversible and controllable way by promoting the catalytic activity of the catalyst electrode for the hydrogenation reaction.

As discussed above, there are several differing methodologies for converting $H_2S$ and $CO_2$ into more useful products. However, these methodologies are time and energy intensive and are generally carried out in separate equipment and/or at separate operating conditions. However, it has been found that a common condition may be used to unite the two methodologies in a more efficient and less energy intensive way. As discussed above, $CO_2$ conversion generally requires $H_2$ to hydrogenate the $CO_2$ thereby forming more useful products. The hydrogen source for hydrogenating $CO_2$ is generally obtained from splitting $H_2O$. As discussed in embodiments below, combining the $H_2S$ treatment—where $H_2$ and elemental sulfur are produced with only 17% of the energy needed to split $H_2O$—and the $CO_2$ hydrogenation, where $H_2$ is required, creates efficiencies for both processes while reducing the total amount of energy and reaction units required to treat $H_2S$ and $CO_2$.

The embodiments disclosed below can be used in any industry where treatment of $H_2S$ and $CO_2$ is desired. For example, in processes where $CO_2$ and $H_2S$ are produced separately, the two streams can be combined and treated in the various embodiments disclosed below, or the two streams may be fed to different portion of an electrolyzer, as disclosed in other embodiments below. However, embodiments are particularly useful in the oil and gas processing industries where high levels of $CO_2$ and $H_2S$ are produced, and where sour gas, which naturally comprises both $CO_2$ and $H_2S$, is refined. For instance, an oil refinery may produce about 700 Mt/yr $CO_2$ and 70 Mt/yr $H_2S$, which are currently converted at about 4%. Embodiments disclosed herein can increase that conversion percentage and undertake the conversions using less energy and reaction units.

Various embodiments disclosed herein comprise electrochemically splitting $H_2S$ in high temperature proton conducting solid oxide electrolyzers for in situ, parallel conversion of $CO_2$ over a catalytic cathode. Further details of embodiments will be disclosed with reference to the figures below.

Figure 3:
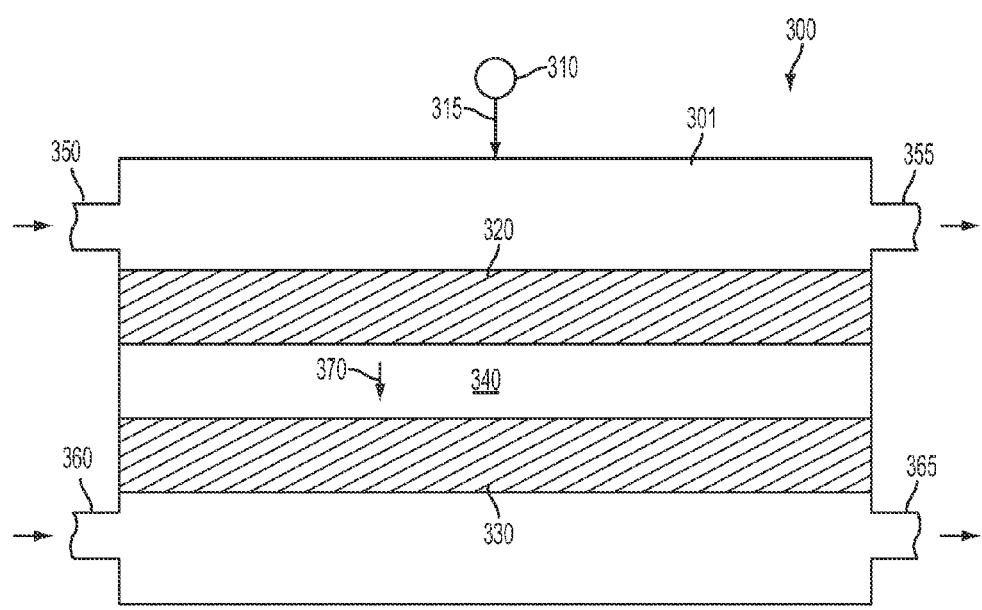
FIG. 3 schematically depicts an electrolyzer for co-processing $H_2S$ and $CO_2$ according to embodiments described herein.

With reference to FIG. 3, embodiments include an electrolyzer 300 comprising a housing 301. The housing comprises inlets 350 and 360 and outlets 355 and 365. In embodiments, the electrolyzer 300 comprises an anode 320, a proton-conducting electrolyte 340, and a cathode 330 encased within the housing 301. Electric current may be applied to the electrolyzer 300 by a current source 310 via an electrical connection 315.

In the embodiment shown in FIG. 3, a gaseous feed stream comprising $H_2S$ and gaseous feed stream comprising $CO_2$ are fed to the electrolyzer 300 in separate feed streams. The feed stream comprising gaseous $H_2S$ is fed to the anode 320 of the electrolyzer 300 through the inlet 350 in the housing 301. The gaseous $H_2S$ is split at the anode 320 into elemental sulfur (also referred to herein as $S_n$, where n=1, 2, 6, or 8) and $H^+$, as shown in Reaction (5) above. The elemental sulfur exits the electrolyzer 300 as an exhaust gas stream at outlet 355 in the housing 301. Simultaneously, the feed stream comprising gaseous $CO_2$ is fed to the cathode 330 of the electrolyzer 300 through the inlet 360 in the housing 301. The $H^+$ ions, which are generated at the anode 320, are transferred through the proton-conducting electrolyte 340, as indicated by arrow 370, to the cathode's 330 three phase boundary (tpb) comprising the cathode 330, the proton-conducting electrolyte 340, and the gaseous phase ($CO_2$ and corresponding reactants). The $H^+$ ions react at the three phase boundary with $CO_2$ adsorbates present at the proximity of the three phase boundary to form various chemicals (such as methane and methanol), as shown in Reaction (16) below:

$$xCO_2\,(ads) + 2(2x-z+y/2)H^+\,(el) + 2(2x-z+y/2)e^- \xrightarrow{tpb} C_xH_yO_z\,(g) + (2x-z)H_2O\,(g). \quad (16)$$

The $C_xH_yO_z$ component then exits the electrolyzer 300 from the outlet 365 as an exhaust gas stream at outlet 365 in the housing 301, where it can be collected for further use. The above Reaction (16) can take place at temperatures from about 200° C. to about 800° C. depending on the desired product. However, in embodiments, temperatures below 700° C. are preferable. The process pressure of Reaction (16) can vary from about 1 atm to about 70 atm, which is similar to the process pressure in methanol synthesis and Fischer-Tropsch reactors. In embodiments, equal pressure is applied to the anode side, and the feed flow is adjusted according to the activity of the catalyst given the desired conversion and reactor size. However, in embodiments, space velocities in the range from about 500 $h^{-1}$ to about 30,000 $h^{-1}$ can be used.

In some embodiments, in addition to, or as an alternative of, Reaction (16), the $H^+$ ions react with one another to form gaseous $H_2$ that may participate in the catalytic hydrogenation of $CO_2$, which is shown in Reactions (12) and (13).

The ratio of catalytic hydrogenation by gaseous $H_2$ (as shown in Reactions (12) and (13)) and electrocatalytic hydrogenation by $H^+$ (as shown in Reaction (16)) is a function of process parameters, such as pressure, temperature, feed flow, etc. For example, $H_2$ evolution at the cathode is suppressed at high pressures and low temperatures and thus atomic hydrogen coverage of the cathode catalyst electrode is higher, which can result in higher $CO_2$ hydrogenation rates. However, the ratio of catalytic/electrocatalytic hydrogenation may also be affected by the catalyst electrode properties, such as $CO_2$ surface dissociation/activation ability. Accordingly, in embodiments, selecting the appropriate cathode material can be important. In some embodiments, typical cathode materials, such as Rh, Ru, Cu, Fe, Co, Pd, Pt, Ni can be used either as metal porous electrodes or as cermet electrodes when mixed with a ceramic electrolyte support (oxygen or proton conductor), like YSZ, ScSZ, ScYSZ, GDC, CGO, $CeO_2$, $TiO_2$, $Nb_2O_5$, SDC, BCY, BZY, CZI, BCN, etc, due to their well known activity in $CO_2$ hydrogenation.

Water present at the cathode 330, such as the $H_2O$ formed by Reactions (12), (13), and (16), will facilitate proton transfer 370 across the electrolyte 340. In some embodiments the generation of water will not be sufficient to facilitate proton transfer 370 across the electrolyte 340. In such cases, humidified $CO_2$ may be fed to the electrolyzer 300. Using water from humidified $CO_2$ to facilitate transfer of protons 370 across the electrolyte 340 may increase the efficiency of the process because an in-line dehumidifier will not be required. In embodiments, the feed stream comprising $CO_2$ may comprise from about 2% to about 15% gaseous $H_2O$, such as from about 3% to about 10% gaseous $H_2O$, or even from about 5% to about 8% gaseous $H_2O$. The exact amount of $H_2O$ in the humidified $CO_2$ feed depends on the electrolyte material 340 and the current applied to the anode 320 and the cathode 330. Like the anode 320, in embodiments, the electrolyte also must be able to tolerate sulfur exposure without significant degradation. Accordingly, in embodiments, the electrolyte 340 may include perovskite materials of the general type $ABO_3$ and $ABMO_3$ that exhibit proton conductivity at high temperatures (600-1000° C.), zirconia- and ceria-based proton conducting electrolytes, like $SrZrO_3$, NiO-doped BZY, $BaCeO_3$, $SrCeO_3$ or others like YDC, SDC, BCY, BCN and CZI. In yet other embodiments, the electrolyte may be a solid acid of the general type $MHXO_4$ and $M_3H(XO_4)_2$, where M can be Cs, $NH_4$, Rb, and X can be S or Se. These materials exhibit protonic conductivity at low temperatures, in the range 25 to 300° C. and are known to undergo a "superprotonic" phase transition.

In some embodiments, the electrolyte 340 may not require $H_2O$ to facilitate the transfer of protons 370 across the electrolyte 340. Like the anode 320, in embodiments, the electrolyte also must be able to tolerate sulfur exposure without significant degradation. For example, Ni-doped BZY does not require $H_2O$ at all, and the above categories of proton conducting electrolytes exhibit an adequate sulfur tolerance.

Anode 320 materials are directly exposed to $H_2S$ and, thus, the anode 320 materials are selected that are highly resistant to sulfur degradation. In embodiments, the anode 320 may comprise $Li_2S/CoS_{1.35}$ or $WS_2$, NiS, $MoS_2$, CoS, $VO_5$, $LiCoO_2$, $Pt/TiO_2$, Pd, Au, Ag, Ru, Rd, Ir, FeMoS, NiMoS, CoMoS and mixtures of them. Also, Ni-based materials like $Nb_2O_5$—Ni, BaO—Ni, $Ce_{0.8}Sm_{0.2}O_2$—Ni. Thiospinels like: $CuFe_2S_4$, $CuNi_2S_4$, $CuCoS_4$, $NiCo_2S_4$, $NiFe_2S_4$, and mixed metal oxides of La, Sr, Mn, Ti, Cr, Ga, Y, V, Fe, Co, Mo, Ce, Mg, Gd, Ba, e.g. $La_{0.4}Sr_{0.6}BO_3$ where B=Mn, Ti, Cr. Most of the above mentioned materials have been reported to exhibit electrochemical activity for $H_2S$ utilization in both fuel cells and electrolyzers. These materials can be used either as is or in mixture with another oxide in the form of ceramic-metallic (cermet) electrode. Oxides that conduct oxygen or protons can be used such as YSZ, ScSZ, ScYSZ, GDC, CGO, $CeO_2$, $TiO_2$, $Nb_2O_5$, SDC, BCY, CZI, BCN, etc.

In some embodiments, the electrolyzer 300 is used downstream of a $CO_2$ capture unit where high purity $CO_2$ is available to feed to the cathode 330 of the electrolyzer 300. Although the embodiment shown in FIG. 3 is discussed above as a solid oxide electrolyte electrolysis unit, it should be understood that in other embodiments, other proton conducting membrane electrolyzers may be used (such as $CsHSO_4$) as long as the anode and electrolyte have sufficient sulfur tolerance, and the cathode is capable of $CO_2$ activation.

Figure 4A:
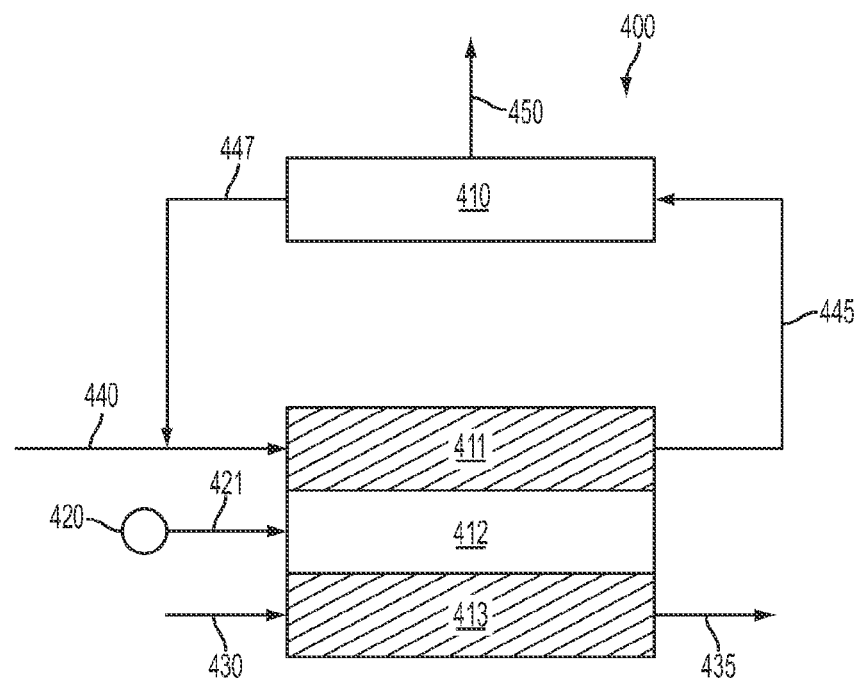
FIG. 4A schematically depicts a second electrolyzer for co-processing $H_2S$ and $CO_2$ according to embodiments described herein.
Figure 4B:
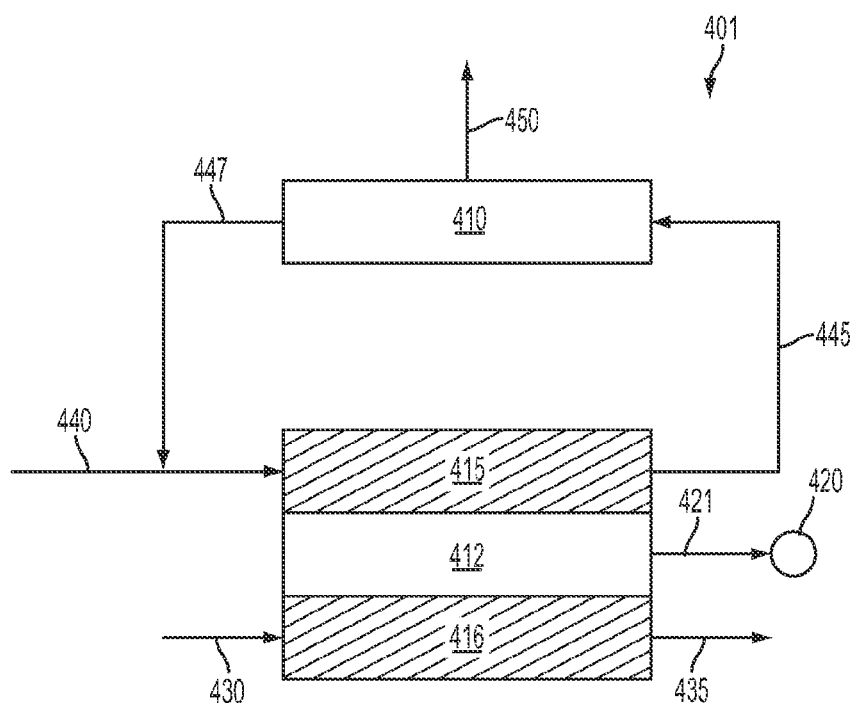
FIG. 4B schematically depicts a $H_2S$ fuel cell according to embodiments described herein.

FIG. 4A and FIG. 4B schematically depict embodiments where $H_2S$ and $CO_2$ are co-fed to an electrolyzer and a fuel cell respectively. In the embodiments disclosed in FIG. 4A and FIG. 4B, CO assists in removing the hydrogen from $H_2S$. In FIG. 4A, the electrolyzer 400 comprises an anode 411, a cathode 413, and an electrolyte between, and in electrochemical communication with, the anode 411 and the cathode 413. Electrical current is provided by an electrical source 420 and fed to the electrolyzer, such as fed to the anode, via an electrical connection 421.

A feed stream comprising $H_2S$ 440 is mixed with a stream comprising CO 447 and the mixture is fed to the anode 411 of the electrolyzer 400. In some embodiments, the anode 411 may comprise a metal sulfide catalyst. In embodiments, the metal sulfide catalyst-anode may be of a group of metal sulfides exhibiting high activity for the Reaction (17) and also low overpotential for hydrogen oxidation (reverse Reaction (6)), like $Co_9S_8$, NiS, FeS, MnS, $Cr_2S_3$, ZnS, $MoS_2$, $Cu_2S$, $V_3S_4$, $Ti_5S_4$, $WS_2$, or thiospinels like: $CuFe_2S_4$, $CuNi_2S_4$, $CuCoS_4$, $NiCo_2S_4$, $NiFe_2S_4$ or mixtures thereof. These materials can be used either as is or in mixture with another oxide in the form of ceramic-metallic (cermet) electrode. Oxides that conduct oxygen or protons can be used such as YSZ, ScSZ, ScYSZ, GDC, CGO, $CeO_2$, $TiO_2$, $Nb_2O_5$, SDC, BCY, CZI, BCN, etc. At the anode, $H_2S$ in the mixture reacts with CO in the mixture to form carbonyl sulfide (COS) and hydrogen, as shown in Reaction (17) below:

$$H_2S + CO \rightarrow H_2 + COS \qquad (17).$$

In the embodiment shown in FIG. 4A, the COS exits the anode 411 of the electrolyzer as exhaust gas stream 445. The COS is then fed to a decomposer 410 where the sulfur is separated from the CO in the COS at high temperatures in the range from about 600° C. to about 1000° C. and pressure from about 1 atm to about 50 atm. The decomposition reaction can be easily integrated thermally with the electrochemical device (electrolyzer or fuel cell) since they operate at a similar temperature range. Sulfur is released as elemental sulfur ($S_n$) 450 from the decomposer 410 and CO exits the decomposer as feed stream 447 and is recycled by being combined with the $H_2S$ feed 440. The decomposition of COS into CO and $S_n$ proceeds by Reaction (18) below:

$$COS \rightarrow CO + 1/nS_n \quad (18).$$

By supplying an electrical current to the electrolyzer 400, $H_2$ will be oxidized at the anode 411 and transferred as protons ($H^+$) across the electrolyte 412 to the cathode 413 where molecular or gaseous hydrogen will be produced. In some embodiments, there is no additional feed to the electrolyzer (i.e., feed 430 is not present) and the molecular or gaseous hydrogen will be released from the electrolyzer 400 as outlet feed 435.

In other embodiments, $CO_2$ may be fed to the cathode 413 as feed stream 430. In these embodiments, the $H^+$ that is formed at the anode 411 and transferred across the electrolyte 412 will react at the triple phase boundary of the gaseous phase, the cathode 413, and the electrolyte, as shown in Reaction (16) above. Through Reaction (16), $C_xH_yO_z$ is produced at the cathode and exits the electrolyzer as exhaust stream 435.

In the embodiment shown in FIG. 4B, electricity is produced by feeding oxygen or air as feed stream 430 to the electrode 416. In such embodiments, the hydrogen that is formed at the electrode 415 and transferred across the electrolyte 412 undergoes electrochemical reduction at the electrode 416. Although electrode 415 and electrode 416 may have the same compositional makeup as anode 411 and cathode 413 of the embodiments shown in FIG. 4A, because hydrogen is reduced at electrode 416, in the embodiment shown electrode 416 is referred as an cathode and electrode 415 is referred to as a anode when referring to the embodiment shown in FIG. 4B.

In FIG. 4A of these embodiments, a feed stream comprising $H_2S$ 440 is mixed with a feed stream comprising CO 447 and the mixture is fed to the anode 415 of the electrolyzer 400. In some embodiments, the anode 411 may comprise a metal sulfide catalyst. In embodiments, the metal sulfide catalyst may be of a group of metal sulfides exhibiting high activity for the Reaction (17) and also low overpotential for hydrogen oxidation (reverse Reaction (6)), like $Co_9S_8$, NiS, FeS, MnS, $Cr_2S_3$, ZnS, $MoS_2$, $Cu_2S$, $V_3S_4$, $Ti_5S_4$, $WS_2$ or thiospinels like: $CuFe_2S_4$, $CuNi_2S_4$, $CuCoS_4$, $NiCo_2S_4$, $NiFe_2S_4$ or mixtures thereof. In some embodiments, the cathode 413 comprises a catalyst, such as Pt, Pd, Ru, Rh, Ni, Cu, Fe, Co or other metals well known for hydrogen evolution in electrolyzers literature either as metal porous electrodes or as cermet electrodes when mixed with a ceramic electrolyte support (oxygen or proton conductor), like YSZ, ScSZ, ScYSZ, GDC, CGO, $CeO_2$, $TiO_2$, $Nb_2O_5$, SDC, BCY, BZY, CZI, BCN, etc, or even a perovskite electrode. At the anode 411, $H_2S$ in the feed stream reacts with CO in the feed stream to form carbonyl sulfide (COS) and hydrogen, as shown in Reaction (17) above. In embodiments, the COS exits the anode 411 of the electrolyzer as outlet stream 445. The COS is then fed to a decomposer 410 where the elemental sulfur is separated from the CO in the COS at elevated temperatures. The elemental sulfur released as elemental sulfur ($S_n$) 450 from the decomposer 410 and CO exits the decomposer as outlet stream 447 and is recycled by being combined with the feed stream comprising $H_2S$ 440. The decomposition of COS into CO and $S_n$ proceeds by reaction (18) above.

In embodiments, the hydrogen that is formed at the anode 415 and transferred across the electrolyte 412 is oxidized by the oxygen or air that is introduced to the cathode 416 as feed stream 430, and $H_2O$ is released as exhaust stream 435. In such embodiments, the electrolyzer 400 operates as a fuel cell and produces electricity by oxidizing the hydrogen is produced from the $H_2S$—CO cycle present at the anode. The electricity generated by oxidizing the hydrogen exits the fuel cell 401 via electrical connection 421 and is sent to an electrical device 420.

In either of the embodiments shown in FIG. 4A or FIG. 4B, removal of $H_2$ from the electrolyzer 400 or the fuel cell 401 during the $H_2S$—CO cycle has a synergistic effect on system performance. Particularly, removing the $H_2$ improves the extent of the $H_2S$—CO reaction toward higher conversions (i.e., higher $H_2$ production) and it will prevent the $H_2$ from reacting with the CO in outlet stream 447 to form methane and water, which if formed can poison the catalyst present at the anodes 411 or 415. The embodiments shown in FIG. 4A and FIG. 4B may also avoid having elemental sulfur deposit on the anodes 411 or 415, which is costly to remove.

In other embodiments, the electrolyzer shown in FIG. 4A can be used to generate high pressure hydrogen. When the anode 411 potential is higher than the minimum required potential, hydrogen is not only pumped from the anode 411, but it can also be generated at high pressures at the cathode 413 according to the Nernst equation, which is $E=E°+(RT/nF)\ln(P_{H2,cathode}/P_{H2,anode})$, where E is the applied potential, E° is the standard cell potential (E°=0V in his case), R is the universal gas constant, T is the absolute temperature, F is the Faraday constant, n is the number of electrons transferred in the cell half-reaction, $P_{H2,cathode}$ is the partial pressure of hydrogen at the cathode, and $P_{H2,anode}$ is the partial pressure of hydrogen at the anode. In embodiments where hydrogen is generated at the cathode 413, no feed 430 to the cathode is required. The concentration of hydrogen at the anode 411 may be controlled by the equilibrium of the reaction between $H_2S$ and CO. However, the partial pressure of hydrogen at the cathode is dependent on the applied electrode potential. The higher of the applied electrode potential, the higher the pressure of hydrogen at the cathode is. High pressure hydrogen is desirable for use in further processes. Potential values up to the reduction potential of the used electrolyte ($E_{red}$=2.3V for YSZ) at the operation temperature can be applied regardless the system pressure, while the generated hydrogen partial pressure is limited to the operation pressure of the system. For example, in embodiments, at 900° K and atmospheric pressure operation and 20% conversion of $H_2S$, 20 kPa hydrogen exists at the anode. The generation of 20 kPa at the cathode is spontaneous and thus no potential difference is needed. However, the generation of 100 kPa hydrogen at the cathode would theoretically require the application of 0.062V potential difference at the cell according to Nernst equation.

Embodiments may also include introducing a hydrogen source into an electrolyzer at the cathode. Referring now to the embodiment shown in FIG. 5, an electrolyzer 500 includes a housing 501 having inlet channels 560 and 570 and outlet channels 565 and 575. Positioned within the housing are an anode 520, a cathode 530, and an electrolyte 540 positioned between, and in electrochemical contact with, the anode 520 and the cathode 530. In the embodiments shown in FIG. 5, a feed stream comprising $H_2S$ is fed to the anode 520 of the electrolyzer 500 via inlet channel 560 in the housing 501. The H$_2$S is split into elemental sulfur and hydrogen as shown in Reaction (5) above. The elemental sulfur exits the electrolyzer 500 at outlet channel 565 in the housing 501. An electrical current is provided by current source 510 to the anode by electrical connection 515. The electrical current is provided to the anode 520 and disassociates hydrogen into H$^+$ ions that are transferred across the electrolyte 540 to the cathode 530, as shown by arrow 550. Minimum potential required for H$_2$S electrolysis is 0.2 V. A feed stream comprising a mixture of CO$_2$ and H$_2$ is fed to the cathode 530 of the electrolyzer 500 via inlet channel 570 providing an additional hydrogen source for the hydrogenation of CO$_2$. The H$^+$ ions formed at the anode 520 and transferred across the electrolyte 540 form promoting species on the surface of cathode 530 that promote hydrogenation of CO$_2$ with the hydrogen supplied with the feed at inlet channel 570. By forming the promoting species, the CO$_2$ hydrogenation rate can be significantly improved. For example, it has been found that faradaic efficiency values of about 900 times higher than the value without promoting species, such as about 950 times higher than the value without promoting species, or even about 1000 times higher than the value without promoting species have been realized using the promoting species. Hydrogen can also be fed to the anode in the embodiments shown in FIG. 4A, which is described in more detail above. In this instance, the minimum applied potential in the electrolyzer is 0 V.

Figure 7A:
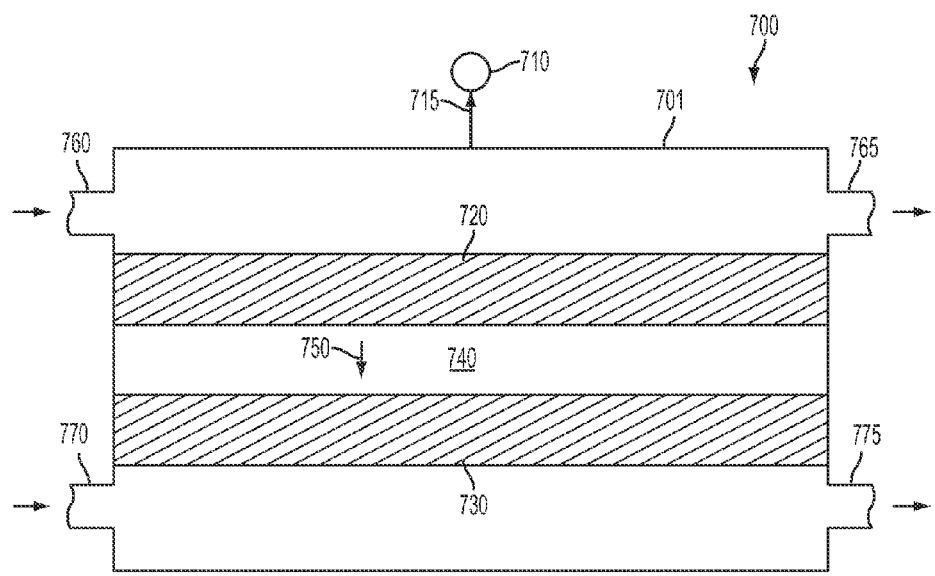
FIG. 7A schematically depicts a fifth electrolyzer for co-processing $H_2S$ and $CO_2$ according to embodiments described herein.

FIG. 7A is an embodiment showing an electrolyzer where CO$_2$ is used to aid in the sulfur removal. In the embodiment of FIG. 7A, an electrolyzer 700 is shown including a housing 701 having inlet channels 760 and 770 and outlet channels 765 and 775. Within the housing are an anode 720, a cathode 730, and an electrolyte 740 positioned between, and in electrical contact with, the anode 720 and the cathode 730. As discussed in further detail below, a feed stream comprising CO$_2$ is introduced at inlet channel 760 to aid in the removal of sulfur.

When oxygen-ion solid electrolyte membranes are used in H$_2$S-powered fuel cells, two mechanisms for sulfur removal from the anode 720 surface are used: 1) the sulfur electrochemical oxidation to gaseous SO$_x$; and 2) the formation of elemental sulfur. The formation of elemental sulfur is common in electrochemical cells equipped with proton (H$^+$) conducting membranes, and SO$_x$ is not formed. However, under high current densities and H$_2$S concentrations, a significant amount of elemental sulfur (S$_n$) is produced at the anode, which creates a situation where sulfur removal is desired. In embodiments, sulfur may be removed by introducing a feed stream comprising CO$_2$ to function as an oxidant at the anode 720, which facilitates the removal of sulfur species by forming SO$_2$, as shown in Reaction (19) below:

$$2CO_2(g)+S(g)\rightarrow SO_2(g)+2CO(g) \qquad (19).$$

Figure 8A:
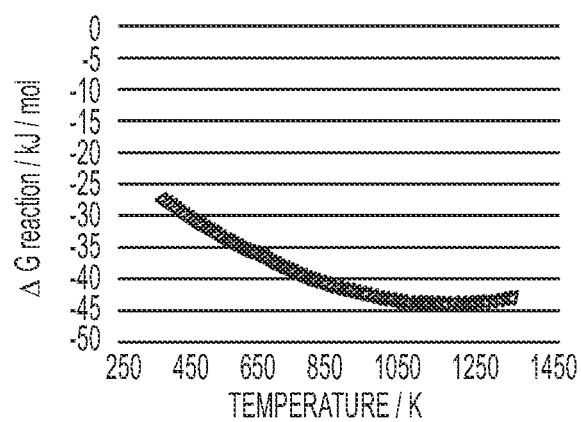
FIG. 8A is a graphical representation of the Gibbs free energy for a reaction between elemental sulfur and $CO_2$.
Figure 8B:
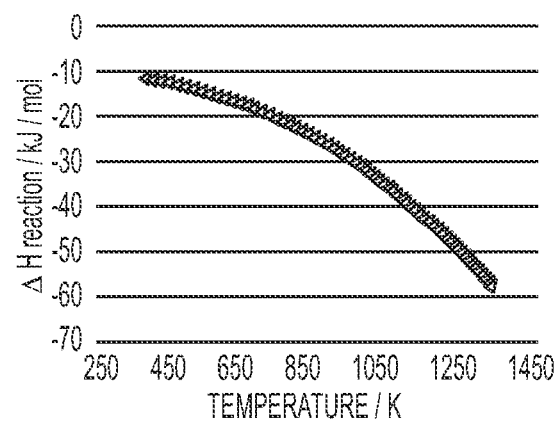
FIG. 8B. is a graphical representation of enthalpy for a reaction between elemental sulfur and $CO_2$.

As shown in FIG. 7A, a feed stream comprising a mixture of CO$_2$ and H$_2$S is fed to the anode 720 of the electrolyzer 700 via inlet channel 760. H$_2$S is electrolyzed to hydrogen and sulfur, while the gaseous CO$_2$ and sulfur react according to Reaction (19) to form CO and SO$_2$, which exit the electrolyzer 700 at outlet channel 765. As shown in FIG. 8A and FIG. 8B, where the enthalpy and Gibbs free energy of Reaction (19) are shown as a function of temperature, Reaction (19) appears to be spontaneous (as indicated by Gibbs free energy below 0) and slightly exothermic (as shown by enthalpy below 0). Thus, it is very likely that at high temperatures, CO$_2$ will dissociate to gaseous CO and atomic oxygen adsorbed on the anode surface that will oxidize sulfur to gaseous SO$_2$. In embodiments, the temperatures for dissociating CO$_2$ are from about 250 to about 1300° K, such as from about 500 to about 1000° K, or even from about 600 to about 800° K.

In further embodiments, the hydrogen H$_2$ dissociated from the H$_2$S will be disassociated into H$^+$ ions when an electrical current is applied to the anode 720. The electrical current may be provided via an electrical device 710 and an electrical connection 715. The H$^+$ ions will transfer across the electrolyte 740, as indicated by arrow 750, to the cathode 730. In the embodiments shown in FIG. 7A, a feed stream comprising CO$_2$ is fed to the cathode 730 of the electrolyzer 700 via inlet channel 770. The CO$_2$ reacts with the hydrogen according to Reaction (16) at the three phase boundary to form C$_x$H$_y$O$_z$ that exits the electrolyzer 700 at outlet channel 775.

Figure 7B:
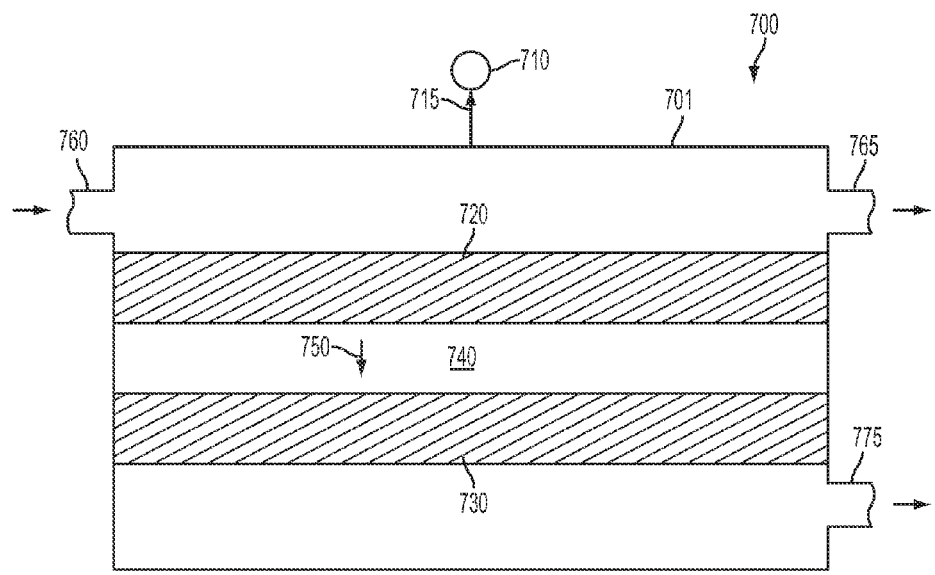
FIG. 7B schematically depicts a second $H_2S$ fuel cell according to embodiments described herein.

FIG. 7B shows an embodiment comprising a fuel cell using CO$_2$ to aid removal of sulfur. In the embodiment of FIG. 7A, an electrolyzer 700 is shown including a housing 701 having inlet channels 760 and 770 and outlet channel 775. Within the housing are an anode 720, a cathode 730, and an electrolyte 740 positioned between, and in electrochemical communication with, the anode 720 and the cathode 730. As discussed above with reference to FIG. 7A, a feed stream comprising CO$_2$ is fed to the anode 720 of the fuel cell 700 via inlet channel 760 to aid in the removal of sulfur.

In the embodiment shown in FIG. 7B, a feed stream comprising a mixture of CO$_2$ and H$_2$S is fed to the anode 720 of the electrolyzer 700 via inlet channel 760. The gaseous CO$_2$ and sulfur react according to Reaction (19) to form CO and SO$_2$, which exit the electrolyzer 700 at outlet channel 765.

In embodiments, the hydrogen dissociated from the H$_2$S will transfer across the electrolyte 740, as indicated by arrow 750, to the cathode 730. In the embodiments shown in FIG. 7B, O$_2$ or air is fed via inlet channel 770 that reacts with H$^+$ at the cathode and water is formed which exits the electrolyzer 700 at outlet channel 775, and electricity is generated in the fuel cell from the transfer of protons across the electrolyte and sent from the fuel cell to an electrical device 710 via an electrical connection 715.

EXAMPLES

Embodiments will be further clarified by the following example and comparative example.

Example

Figure 5:
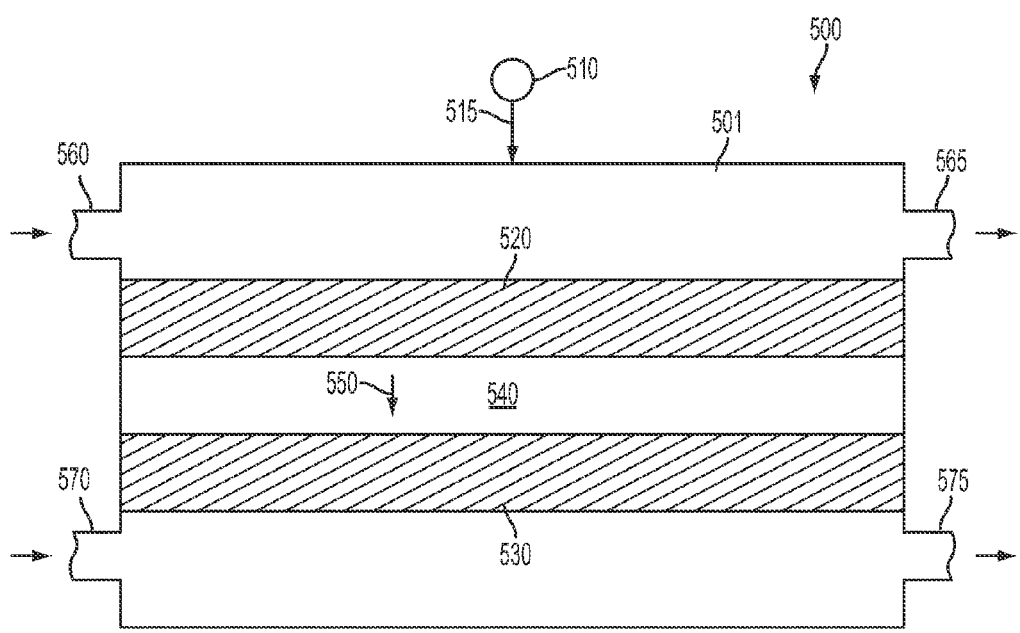
FIG. 5 schematically depicts a third electrolyzer for co-processing $H_2S$ and $CO_2$ according to embodiments described herein.

In this example the electrical power required to hydrogenate a maximum possible amount of CO$_2$ to CH$_4$ is calculated. For this example, an electrochemical reactor as shown in FIG. 5 is integrated into a refinery or other gas plant that has the following specifications: H$_2$S mass flow rate of 1 ton/h; CO$_2$ mass flow rate of 1 ton/h; and the required H$_2$S conversion is 100%. From the above, it is estimated (from stoichiometric calculations) that from each ton of H$_2$S, 0.94 ton/h of elemental sulfur and 0.059 ton/h of H$_2$ can be generated by electrochemical splitting by aiming for 100% H$_2$S elimination.

The above requires 2×0.059=0.118 ton H$^+$/h or 16.3 mol H$^+$/s through the proton conducting electrolyte membrane, which is equivalent to a 1573 kA current and 3.3 MW power, assuming that the electrolysis unit operates at about 2.1 V (this assumption is based on about 0.2 V anode overpotential and 1.9 V cathode overpotential (according to H$_2$S electrochemical oxidation and $CO_2$ electrochemical reduction studies), and the Faradaic efficiency reaches 100%).

Using the above numbers and assuming that all H+ are used to hydrogenate $CO_2$ and not to form $H_2$ gas, 0.117 ton/h $CH_4$ and 0.53 ton/h $H_2O$ are produced, which corresponds to about 32% conversion of $CO_2$ in the total $CO_2$ fed to the reactor. If the desired product is $CH_3OH$ rather than $CH_4$, the same amount of power (or H+ species) produces 0.31 ton/h $CH_3OH$ and 0.18 ton/h $H_2O$, which corresponds to $CO_2$ conversion of about 43%.

This example shows an estimation of power consumption for the electrochemical system described above and described with respect to FIG. 5. The example also shows the importance of product selection as it is estimated that over 10% more $CO_2$ is converted when methanol is the desired product as opposed to methane. This is believed to be because $CH_3OH$ formation requires less H+ than $CH_4$ formation, which combined with the higher heating value of $CH_3OH$ than $CH_4$ (4 kJ/mol versus 0.75 kJ/mol, respectively) can significantly benefit the economics of the process.

Comparative Example

Figure 6:
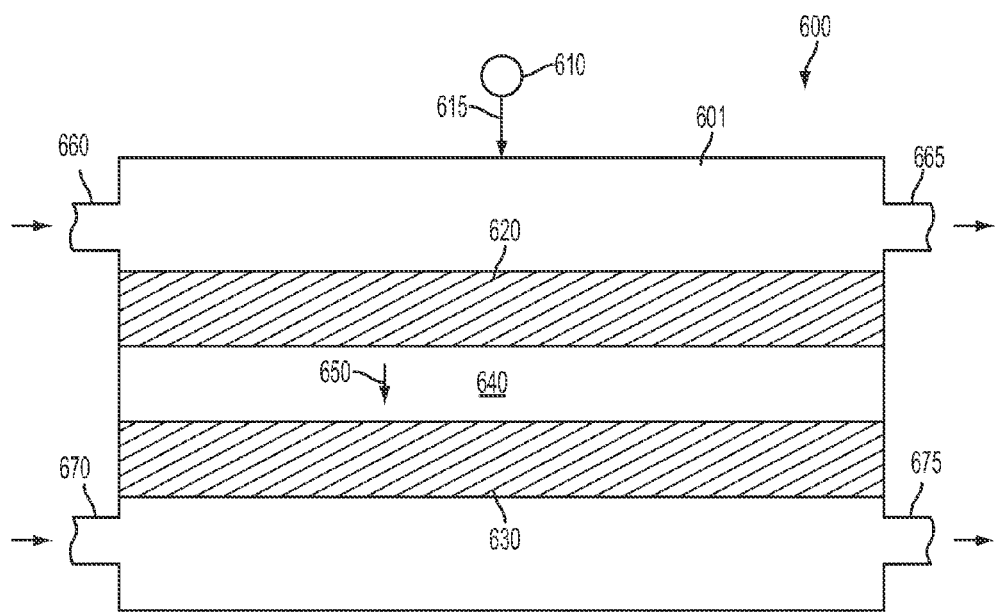
FIG. 6 schematically depicts a fourth electrolyzer for co-processing $H_2S$ and $CO_2$ according to embodiments described herein.

This Comparative Example shows electrolysis using $H_2O$ in place of $H_2S$. With reference now to FIG. 6, an electrolyzer 600 includes a housing 601 having inlet channels 660 and 670 and outlet channels 665 and 675. Positioned within the housing are an anode 620, an electrolyte 640, and a cathode 630. In the embodiments shown in FIG. 6, $H_2O$ is fed to the anode 620 of the electrolyzer 600 via inlet channel 660 in the housing 601. The $H_2O$ is split into elemental oxygen and hydrogen as shown in Reaction (20) below:

$$H_2O(g) \rightarrow 2H^+ + \tfrac{1}{2}O_2(g) + 2e^- \qquad (20).$$

The elemental oxygen exits the electrolyzer 600 at outlet channel 665 in the housing 601. An electrical current is provided by current source 610 to the anode by electrical connection 615. The electrical current is provided to the anode 620 and disassociates water into H+ ions that are transferred across the electrolyte 640 to the cathode 630, as shown by arrow 650. $CO_2$ is fed to the cathode 630 of the electrolyzer 600 via inlet channel 670. At the cathode, $CO_2$ hydrogenation can occur electrochemically, as shown in Reaction (16) or catalytically, as shown in Reactions (9) and (10). The method of this comparative example produces pure $O_2$ as reaction product, which can be used in many different oxidation reactions. However, power demand for $H_2O$ electrolysis is estimated to be about 1.94 MW (i.e., about 6 times higher than that of $H_2S$ electrolysis), since the water reduction potential is 1.23 V vs. 0.2 V for $H_2S$ at ambient conditions.

Thus, various embodiments of methods for co-processing $CO_2$ and $H_2S$ have been described. In the methods, a feed stream comprising $H_2S$ is fed to an anode side of an electrolyzer so that the $H_2S$ is split into hydrogen and elemental sulfur. The hydrogen may then be transferred across an electrolyte to a cathode. A gas stream comprising $CO_2$ is fed at a cathode side of the electrolyzer. The $CO_2$ is hydrogenated by the hydrogen that is transferred across the electrolyte and is hydrogenated into a more useful chemical product, such as methane or methanol. In various embodiments, additional components may be fed to the electrolyzer with the feed streams comprising $H_2S$ and $CO_2$. For example, in some embodiments CO may be fed to the anode side of the electrolyzer with the gas stream comprising $H_2S$ so that the $H_2S$ reacts with the CO at the anode side of the electrolyzer to form COS and $H_2$. In some embodiments, an additional hydrogen source may be fed to the cathode side of the electrolyzer with the $CO_2$ to aid in the hydrogenation of the $CO_2$. Unlike with conventional processes that split $H_2S$ and hydrogenate $CO_2$ separately, co-processing $H_2S$ and $CO_2$ creates efficiencies, such as reducing the number of units required to process $H_2S$ and $CO_2$, by removing the adsorbed sulfur on the anode to the gas phase as $SO_x$, and by using less energy than processes that treat $H_2S$ and $CO_2$ separately.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A method for co-processing $H_2S$ and $CO_2$ in an electrolyzer that comprises an anode, a cathode, and an electrolyte positioned between and in electrochemical contact with the anode and the cathode, the method comprising:

feeding a first gas stream comprising $H_2S$ to the anode of the electrolyzer;

feeding a second gas stream comprising $CO_2$ to the cathode of the electrolyzer;

splitting $H_2S$ of the first gas stream into hydrogen and elemental sulfur at the anode;

transferring the hydrogen split from the $H_2S$ of the first gas stream from the anode across the electrolyte to the cathode; and hydrogenating the $CO_2$ from the second gas stream with the hydrogen that was transferred from the anode, wherein the electrolyte is a solid electrolyte; and the elemental sulfur split from the $H_2S$ does not migrate into the electrolyte and is substantially removed from the anode from the electrolyzer as an anode exhaust stream.

2. The method of claim 1, wherein the $CO_2$ from the second gas stream is hydrogenated according to a reaction as follows:

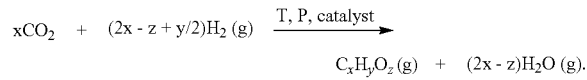

$$xCO_2 + (2x - z + y/2)H_2(g) \xrightarrow{\text{T, P, catalyst}} C_xH_yO_z(g) + (2x - z)H_2O(g).$$

wherein $C_xH_xO_z$ is selected from the group consisting of methane, ethane, propane, methanol, ethanol, and propanol.

3. The method of claim 2, wherein the $CO_2$ from the second gas stream is hydrogenated to form water and one of methane and methanol.

4. The method of claim 1, wherein the anode comprises a metal sulfide.

5. The method of claim 1, wherein the anode comprises a member selected from the group consisting of NiS, $MoS_2$, $WS_2$, CoS, $Li_2S/CoS_{1.35}$, FeMoS, NiMoS, CoMoS, $VO_5$, $LiCoO_2$, $Pt/TiO_2$, Pd, Au, Ag, Ru, Rd, Ir, $Nb_2O_5$—Ni, BaO—Ni, $Ce_{0.8}Sm_{0.2}O_2$—Ni, $CuFe_2S_4$, $CuNi_2S_4$, $CuCoS_4$, $NiCo_2S_4$, $NiFe_2S_4$, and mixed metal oxides of La, Sr, Mn, Ti, Cr, Ga, Y, V, Fe, Co, Mo, Ce, Mg, Gd, and Ba.

6. The method of claim 1, wherein the electrolyte comprises a member selected from the group consisting of perovskite materials of the general type $ABO_3$ and $ABMO_3$ that exhibit proton conductivity at temperatures from 600° C. to 1000° C., zirconia- and ceria-based proton conducting electrolytes, and solid acids of $MHXO_4$ and $M_3H(XO_4)_2$, where M is Cs, $NH_4$, Rb, and X is S or Se.

7. The method of claim 1, wherein CO is added to the first gas stream, and the method further comprises forming carbonyl sulfide.

8. The method of claim 7, wherein the method further comprises feeding the carbonyl sulfide to a decomposer where the carbonyl sulfide is split into elemental sulfur and CO.

9. The method of claim 8, wherein the CO produced in the decomposer by splitting the carbonyl sulfide is the CO added to the first gas stream.

10. The method of claim 1, wherein the second gas stream comprises $CO_2$ and an additional hydrogen source.

11. The method of claim 10, wherein the hydrogen split from the $H_2S$ of the first gas stream is transferred from the anode across the electrolyte and form promoting species on the cathode.

12. The method of claim 1, wherein the first gas stream comprises $H_2S$ and $CO_2$ and the method further comprises forming $SO_x$ and CO after the $H_2S$ in the first gas stream is split into hydrogen and elemental sulfur.

* * * * *

UNITED STATES PATENT AND TRADEMARK OFFICE
CERTIFICATE OF CORRECTION

PATENT NO. : 9,951,430 B2  
APPLICATION NO. : 14/688578  
DATED : April 24, 2018  
INVENTOR(S) : Souentie et al.

Page 1 of 1

It is certified that error appears in the above-identified patent and that said Letters Patent is hereby corrected as shown below:

Column 16, Line 51, Claim 2:
"wherein $C_xH_xO_z$ is selected from the group consisting of"
Should read:
--wherein $C_xH_yO_z$ is selected from the group consisting of--; and Column 16, Line 61, Claim 5:
"$WS_2$, CoS, $Li_2S/CoS_{135}$, FeMoS, NiMoS, CoMoS, $VO_5$,"
Should read:
--$WS_2$, CoS, $Li_2S/CoS_{1.35}$, FeMoS, NiMoS, CoMoS, $VO_5$,--.

Signed and Sealed this  
Thirtieth Day of April, 2019

Andrei Iancu  
*Director of the United States Patent and Trademark Office*